US008491488B1

(12) United States Patent
Criley et al.

(10) Patent No.: US 8,491,488 B1
(45) Date of Patent: Jul. 23, 2013

(54) METHOD AND SYSTEM FOR IDENTIFYING CARDIOPULMONARY FINDINGS BY USING A HEART AND LUNG SOUNDS BUILDER

(75) Inventors: Stuart Ross Criley, Palos Verdes Estates, CA (US); John Michael Criley, Sr., Palos Verdes Estates, CA (US)

(73) Assignee: Blaufuss Medical Multimedia Laboratories, LLC, Rolling Hills Estates, CA (US)

( * ) Notice: Subject to any disclaimer, the term of this patent is extended or adjusted under 35 U.S.C. 154(b) by 0 days.

(21) Appl. No.: 13/252,023

(22) Filed: Oct. 3, 2011

Related U.S. Application Data (60) Provisional application No. 61/389,164, filed on Oct. 1, 2010, provisional application No. 61/542,293, filed on Oct. 3, 2011.

(51) Int. Cl.
*A61B 5/02* (2006.01)

(52) U.S. Cl.
USPC .......................................................... 600/528

(58) Field of Classification Search
USPC .......................................................... 600/528
See application file for complete search history.

(56) References Cited

U.S. PATENT DOCUMENTS

| | | | | |
|---|---|---|---|---|
| 5,687,738 | A * | 11/1997 | Shapiro et al. | 600/528 |
| 5,957,866 | A * | 9/1999 | Shapiro et al. | 600/586 |
| 6,220,866 | B1 | 4/2001 | Amend et al. | |
| 6,527,559 | B2 | 3/2003 | Yoshii et al. | |
| 7,107,095 | B2 * | 9/2006 | Manolas | 600/513 |
| 7,248,923 | B2 | 7/2007 | Maile et al. | |
| 7,424,321 | B2 | 9/2008 | Wariar et al. | |
| 7,438,689 | B2 | 10/2008 | Munk | |
| 7,517,319 | B2 * | 4/2009 | Kushnir et al. | 600/528 |
| 7,559,901 | B2 | 7/2009 | Maile et al. | |
| 7,611,471 | B2 * | 11/2009 | Thiagarajan | 600/528 |
| 7,615,012 | B2 | 11/2009 | Von Arx et al. | |
| 7,645,141 | B2 | 1/2010 | Lecat | |
| 7,662,104 | B2 | 2/2010 | Siejko et al. | |
| 7,670,298 | B2 | 3/2010 | Carlson et al. | |
| 7,736,319 | B2 | 6/2010 | Patangay et al. | |
| 7,780,606 | B2 | 8/2010 | Carlson et al. | |
| 7,806,833 | B2 | 10/2010 | Thiagarajan et al. | |
| 7,853,327 | B2 | 12/2010 | Patangay et al. | |
| 7,883,470 | B2 | 2/2011 | Scheiner et al. | |
| 7,922,669 | B2 | 4/2011 | Zhang et al. | |
| 7,938,781 | B2 | 5/2011 | Carlson et al. | |
| 7,951,087 | B2 | 5/2011 | Siejko et al. | |
| 7,962,210 | B2 | 6/2011 | Daum et al. | |
| 7,972,275 | B2 | 7/2011 | Siejko et al. | |

(Continued)

OTHER PUBLICATIONS

Littman Cardiac Exam Virtual Trainer CD-ROM application manual, 2007.

(Continued)

*Primary Examiner* — Joseph Stoklosa
(74) *Attorney, Agent, or Firm* — Peters Verny, LLP (57) ABSTRACT

A system is provided for creating a sound profile that matches sounds produced by a patient during a physical examination, such as a cardiac or pulmonary examination. A user selects multiple sounds from a library and combines them to form the profile which may then be modified by the addition of further sounds, adjustments to their relative timing, duration, loudness, and so forth. The refinement continues iteratively, and after each change the profile is provided by the system to the user, for example, as a phonocardiogram for comparison against the sounds observed during the examination.

12 Claims, 6 Drawing Sheets

U.S. PATENT DOCUMENTS

| | | |
|---|---|---|
| 8,000,780 B2 | 8/2011 | Wariar et al. |
| 8,007,442 B2 | 8/2011 | Carlson et al. |
| 8,012,098 B2 | 9/2011 | Maile et al. |
| 8,034,000 B2 | 10/2011 | Zhang et al. |
| 8,084,001 B2 | 12/2011 | Burns et al. |
| 8,096,954 B2 | 1/2012 | Stahmann et al. |
| 8,108,034 B2 | 1/2012 | Patangay et al. |
| 8,133,187 B2 | 3/2012 | Holmstrom et al. |
| 8,162,844 B2 | 4/2012 | Carlson et al. |
| 8,167,811 B2 | 5/2012 | Scheiner et al. |
| 8,211,034 B2 | 7/2012 | Patangay et al. |
| 8,277,389 B2 | 10/2012 | Carlson et al. |
| 2004/0092846 A1 | 5/2004 | Watrous |
| 2005/0048455 A1 | 3/2005 | Hayamizu et al. |
| 2005/0119585 A1 | 6/2005 | Watrous |
| 2008/0232605 A1 | 9/2008 | Bagha |
| 2009/0117527 A1 | 5/2009 | Lecat |

OTHER PUBLICATIONS

Adolph, R. J., et al., "Teaching selective attention to the cardiac cycle: The Cardio-gator," Am. Hrt. J., Aug. 1971.

Criley, J.M., "Beyond Heart Sounds, vol. 1" Companion Study Guide, 2000.

Cardionics CardioSim VII Sales Literature, Aug. 2008.

Cardionics CardioSim VII Sales Literature, 1995.

Cardionics Learning Cardiac Auscultation CD-ROM application Sales Literature, 2003.

iMurmur iPhone app Product information, 2010.

iMurmur iPhone app Product information, 2009.

Levinson, D. "A New Audiovisual Aid to Heart-Sound Instruction," JAMA, Sep. 1968.

Easy Auscultation website, http://www.easyauscultation.com/, MedEdu LLC, 2010.

Pinnacle Heart Sounds Tutor website, http://www.pinnacletec.com/medical-training-products/Heart-Sounds-TUTOR.html, 1990.

Cardioscan User Manual, Zargis Medical, 2009.

Vukanovic-Criley, J. M., et al., "Competency in Cardiac Examination Skills in Medical Students, Trainees, Physicians, and Faculty," Arch. Intern. Med., vol. 166, 2006.

Vukanovic-Criley, J. M., et al., "Confidential Testing of Cardiac Examination Competency in Cardiology and Noncardiology Faculty and Trainees: A Multicenter Study," Clin. Cardiol., vol. 33, No. 12, pp. 738-45, 2010.

* cited by examiner

METHOD AND SYSTEM FOR IDENTIFYING CARDIOPULMONARY FINDINGS BY USING A HEART AND LUNG SOUNDS BUILDER

CROSS-REFERENCE TO RELATED APPLICATIONS

This application claims the benefit of U.S. Provisional Patent Application No. 61/389,164 filed on Oct. 1, 2010 and also entitled "Method and System for Identifying Cardiopulmonary Findings by Using a Heart and Lung Sounds Builder;" and the benefit of U.S. Provisional Patent Application No. 61/542,293 filed on Oct. 3, 2011 and entitled "Arterial and Venous Pulsations, Precordial Impulses and Respiratory Pattern Finder," both of which are incorporated herein by reference.

BACKGROUND OF THE INVENTION

Echocardiography was initially developed in the mid-20$^{th}$ Century and its adoption in the subsequent decades has strongly influenced how clinicians are trained and how they subsequently perform cardiac examinations of patients. A readily available, non-invasive method of imaging the beating heart that could provide critical reinforcement of what was heard through the stethoscope should have enhanced physical examination skills, but in fact the opposite has happened. Cardiac examination skills have declined since the advent of echocardiography, a function of overreliance on technology and the present healthcare environment that emphasizes rapid delivery of care. Several decades ago, patients' hospital stays were long, providing trainees and their instructors frequent opportunities for bedside teaching rounds. Today, hospital admissions are short and intensely focused, with fewer opportunities for trainees to learn and practice bedside examination skills Attending physicians, having been trained in this environment, further amplify the problem if their own cardiac examination skills are not well developed. In the absence of bedside training with patients, audio recordings of heart sounds has served as a poor substitute, and as a result clinicians now commonly close their eyes while conducting cardiopulmonary examination, shutting out important visual and palpable cues exhibited by the patient. Multicenter studies of cardiac examination skills document a rise in test scores until the third year of medical school, but no further improvement thereafter despite years in residency training, or even further years in practice. (See, e.g., Arch Intern Med (166):610-617, (2006) and Clin Cardiol (33;12):738-745 (2010)) Indeed, full-time internal medicine professors perform no better in tests of cardiac examination skills than the third-year medical students they teach. Compounding the problem is a lack of critical reinforcement when auscultating patients. Critical reinforcement implies a commitment to confirming or refuting one's bedside diagnostic impressions by critical review and correlation with available imaging and/or hemodynamic studies performed on that patient. Unfortunately, patient exposure without critical reinforcement seems to be the norm for the average medical resident, explaining their lack of advancement in examination skills despite clinical encounters with hundreds of patients.

SUMMARY

This invention relates to audiovisual display on a digital computer system, in particular, visual as well as audio display of cardiac and lung auscultation, allowing the selection of individual sound components to create custom combinations that match the sounds heard from a patient during physical examination with a stethoscope, allowing the selection of different pulsewave contours that match the arterial, venous, or precordial impulses seen on a patient during physical examination, and allowing selection of different respiratory patterns that match the respiration seen and heard from a patient during physical examination.

Various embodiments of the invention are used in human and veterinary medicine as a tool to aid in identification of a patient's cardiopulmonary findings. These embodiments include a computing device configured for selecting a combination of sounds, murmurs, and/or lung sounds, visual examples of arterial, venous, and precordial impulses, and respiratory patterns, and combining the selected sounds and visual examples into an audio and audiovisual sequence. The audio sequence is checked for accuracy by direct comparison to sounds heard in a patient. The video sequence [animation or example patient video] is checked for accuracy by direct comparison with the patient. The selection is quickly refined by an iterative process until a satisfactory match between selected findings and patient findings has been achieved. These findings can be documented locally on the computing device, as well as securely uploaded to a database, and linked to the patient's electronic health record. In some embodiments the computing device is configured to list differential diagnoses based on a user's selection of heart or lung sounds. In some embodiments the computing device is configured to work in reverse, listing diagnoses and then playing the appropriate audiovisual findings, including clinical variations that are encountered across the spectrum of acute versus chronic, mild versus severe, congenital versus acquired. Finally, in some embodiments the computing device is configured to function in a training or testing mode, playing a patient recording, and prompting the user to identify correctly the heart sounds and murmurs, breath and lung sounds, pulsations in the neck and precordium, and respiratory patterns, grading the user entries, and storing the results locally or remotely.

BRIEF DESCRIPTION OF DRAWINGS

FIG. 1.5 is a graphical representation of a control panel provided through a user interface according to various embodiments of the present invention.

DETAILED DESCRIPTION

Figure 1:
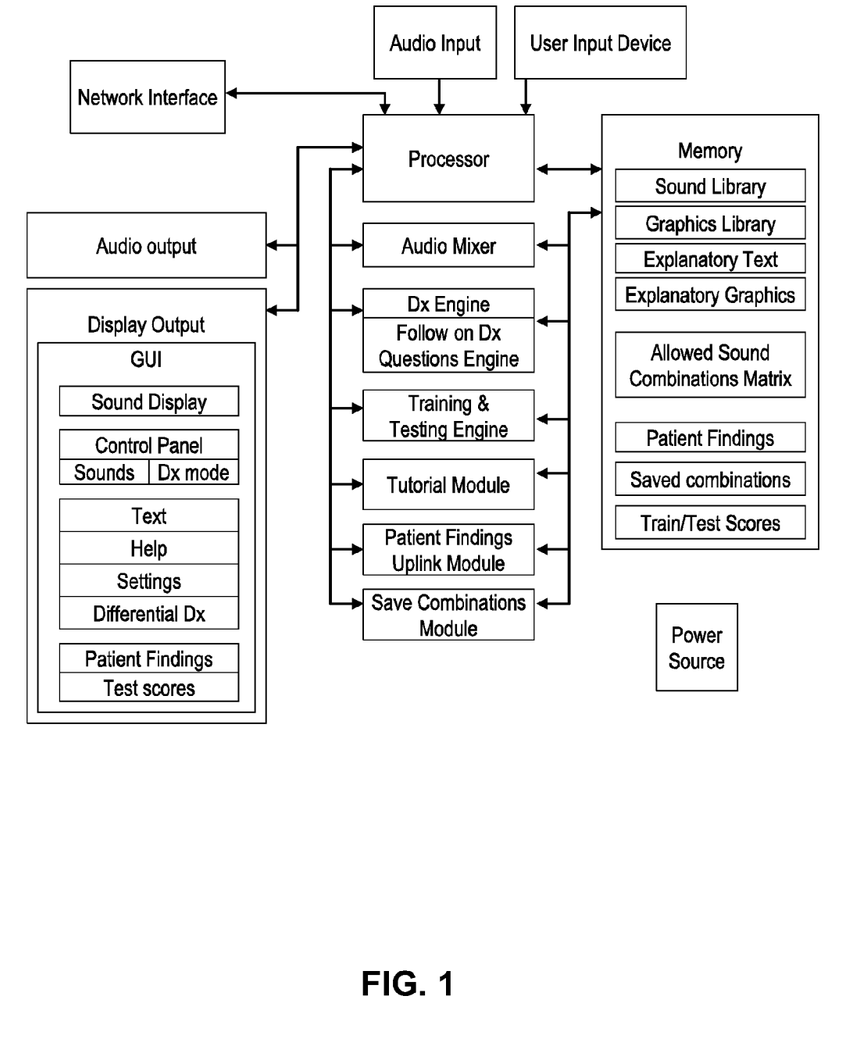
FIG. 1 is a schematic representation of a sound builder system according to various embodiments of the present invention.

FIG. 1 illustrates the general architecture of the sound builder system as embodied in an electronic computing device configured to execute a Sound Builder application. In some embodiments the electronic computing device includes a cellular telephone, digital pad, personal digital assistant, personal computer, and/or the like. Audio input is received from an external source: from a wired audio connection to a microphone and/or stethoscope; from a wireless connection via the Network Interface (e.g., WiFi, Bluetooth, USB); and/or from a live transmission or recorded transmission of a patient recording.

User input is received via a user input device. The user input device uses the user input to select sound components, switch to text, help, settings, or diagnosis sections (Dx) of the Sound Builder application, to submit answers to training/test questions, to record patient findings, or to control the volume, temporal location, tempo of the sound combinations, and/or the like.

In some embodiments, selected sound combinations are checked against an Allowed Combinations Matrix before playing. Combinations may be saved for later recall. Patient findings may be saved and/or uploaded via the Network Interface.

In some embodiments, sound components are recalled from Memory and sent to the Audio Mixer before being sent to Audio Output. The Display Output is updated to reflect the new sound combination chosen by the user.

The following is a step-by-step description of how various embodiments of the invention may be used. The computing device of the invention can be configured to perform some or all of these steps. The various alternatives provided are not meant to be limiting. Other alternatives are considered to be within the scope of the invention.

A user listens to a patient's heart sounds, for example, through an acoustic stethoscope, through an electronic stethoscope, from a received live transmission via computer network, from a recorded transmission via computer network, from a locally stored recording, or from a remotely stored recording. Transmission methods to reach the user's ear include, for example, (1) via headset (wired or wireless) attached or paired to an electronic stethoscope, (2) via headphones (wired or wireless) attached or paired to an electronic stethoscope, (3) via a wired or wireless speaker placed under or attached to an acoustic or electronic stethoscope, and (4) via external audio input and/or electronic interface with the transmitting stethoscope or system.

The user launches the Sound Builder application on the computing device. The Sound Builder application can be implemented in hardware, firmware and/or software store on a computer readable medium and executed by a processor of the computing device. The Sound Builder application optionally comprises a smartphone application, a website-based program, an application installed on a personal computer, an application installed on a personal digital assistant, an embedded application of an electronic stethoscope.

The user selects a sound-murmur combination, for example, by pressing inputs (e.g., on-screen buttons). The sound builder takes the one or more selected audio components and mixes the audio tracks dynamically to create a repeating heart and/or breath sounds. This audio playback optionally continues uninterrupted until a further sound, murmur, or breath sound is added or removed, or until the user halts the playback.

Figure 15:
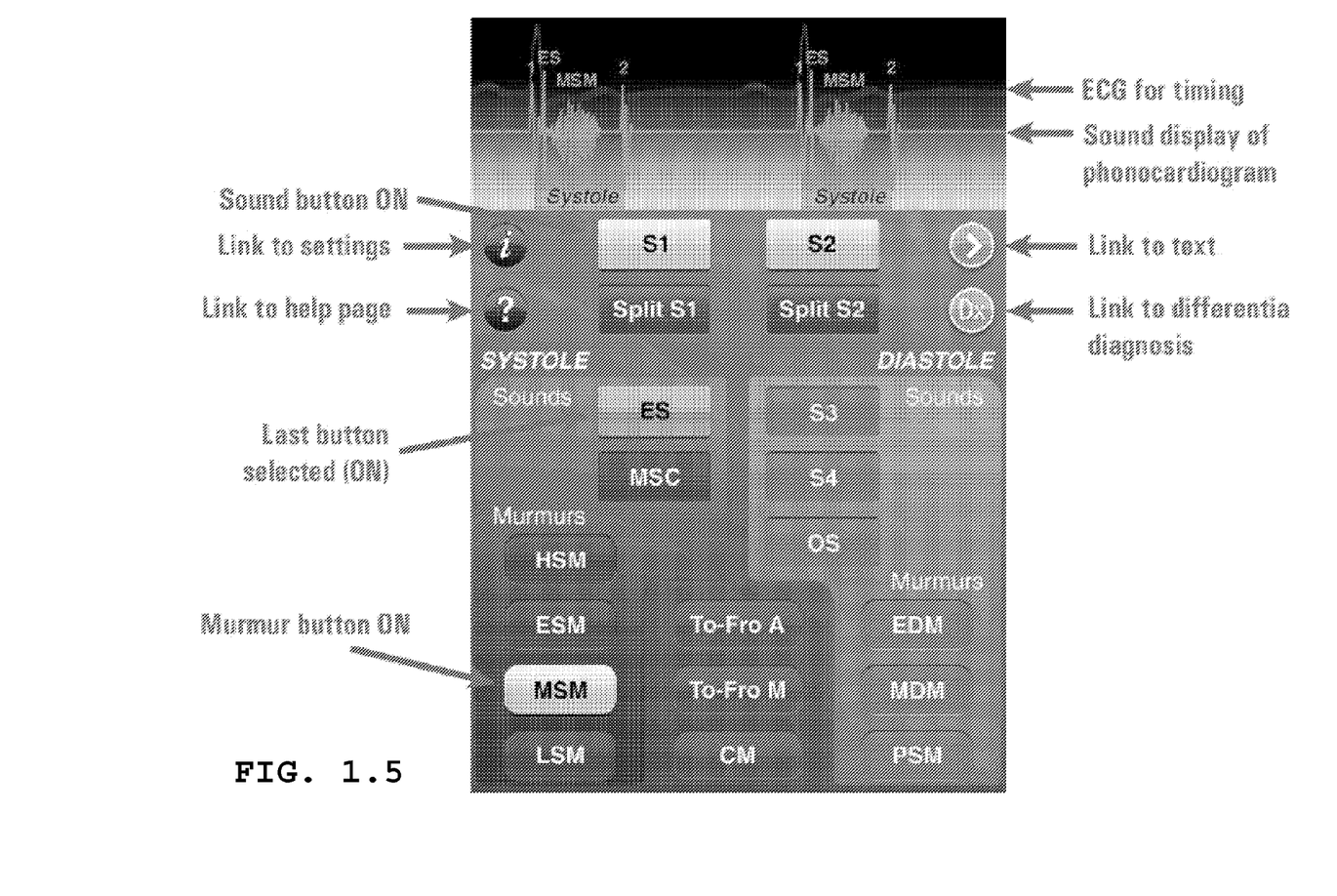

FIG. 1.5 shows an exemplary control panel provided by the Sound Builder application executing on an electronic computing device. In some embodiments, the user starts with a blank slate, or more specifically, a simple S1 S2 combination. By adding sounds or murmurs, a combination of sounds is built up to match what is heard in the patient. Each time a button is selected on the control panel, the sound component is added to the playback, the visual display of the phonocardiogram shows the new component in its proper temporal location, and the selected button lights up to show the user which components are already active.

The Sound Builder application is configured to generate the control panel which provides the user with menus such as a component-based menu and a lesion-based menu. The component-based menu allows the user to select sounds, murmurs, and murmur combinations (e.g., to-fro murmurs) used to create a combination. The lesion-based menu allows the user to select a lesion and optionally to further modify the lesion. Selected lesions can be acute or chronic and vary from mild to severe. The control panel can also be configured to allow the user to vary or specify the heart rate and the listening location.

In various embodiments some or all of the features below can be selected and/or controlled. A first heart sound (S1) is selected, for instance, by recording the location on the patient at which the sound is heard, as the location will influence the sound. Sound components, their loudness, and their relative timings can also be selected for S1. Sound components can be of different types, such as single and split (e.g., physiological, paradoxical, or persistent), loudness can vary from absent to soft to loud, and their timings can be adjusted from early through the expecting timing to late.

Second (S2), third (S3), and fourth (S4) sounds are similarly selected. In some embodiments, the quality of S3 can be selected, such as dull, rumbling, and knocking, and the loudness can be varied from soft to medium to loud. The loudness of S4 can also be varied from soft to medium to loud and the location (left or right ventricular) can be recorded.

Other selectable sounds can include an opening snap (OS), an ejection sound (ES) which can be aortic or pulmonic, and a mild systolic click (MSC). The OS loudness can vary from soft to loud, and the OS timing can be shifted relative to the timing of other sounds. For example, the S2-OS interval can vary either continuously or in discrete steps; shorter intervals—higher left atrial/left ventricular pressure gradient, implying more severe mitral stenosis; and longer intervals—lower left atrial/left ventricular gradient, implying less severe mitral stenosis. The MSC can be selected for the mitral valve or the tricuspid valve. The MSC timing can likewise be shifted relative to the timing of other sounds such that, for instance, the S1-MSC interval can vary, with shorter intervals implying an earlier systolic prolapse, and longer intervals implying a later systolic prolapse. The MSC can be given an accompanying murmur. For example, mitral or tricuspid regurgitation may occur with prolapse, causing a murmur that immediately follows the click. The timing of this murmur depends upon the timing of the click, such that the murmur can be holosystolic, midsystolic, or late systolic.

Other selectable sounds comprise murmurs such as diastolic murmurs, systolic murmurs, and continuous and to-fro murmurs. Selectable diastolic murmurs include early diastolic, mid diastolic, and presystolic murmurs, and as above, for each the location on the patient is specified. For early diastolic murmurs, quality (harsh or high-pitched), shape (decrescendo or crescendo-decrescendo), and duration (long and tapering or short and abruptly terminated) can be selected. For mid diastolic murmurs quality and loudness can be selected, and for presystolic murmurs shape (crescendo), loudness, and accompanying sounds and murmur can be selected. Accompanying sounds and murmur can comprise a mid diastolic murmur, an OS, and a loud S1.

Selectable systolic murmurs include holosystolic, early systolic, mid systolic, and late systolic murmurs, and as above, for each the location on the patient is specified. For each, too, the quality is selectable (harsh, blowing, or musical). The holosystolic shape can be equal intensity, crescendo-decrescendo, or decrescendo. The early systolic and late systolic shapes can be decrescendo, while the mid systolic shape can be equal intensity or crescendo-decrescendo. The duration of the late systolic murmur is also variable.

For continuous murmurs location on the patient is specified. Timing is also controllable as the peak of murmur intensity varies depending upon the etiology. To-fro murmurs comprise semilunar and atrio-ventricular murmurs, both have systolic and diastolic components, and for both the location on the patient is specified. Semilunar to-fro murmurs can be aortic or pulmonic, and either can be characterized as to-FRO (louder diastolic component) or TO-fro (louder systolic component). Aortic to-fro murmurs can also be Austin Flint murmurs, while pulmonic to-fro murmurs can be right-sided Austin Flint murmurs. Atrio-ventricular to-fro murmurs can be mitral or tricuspid.

Figure 2:
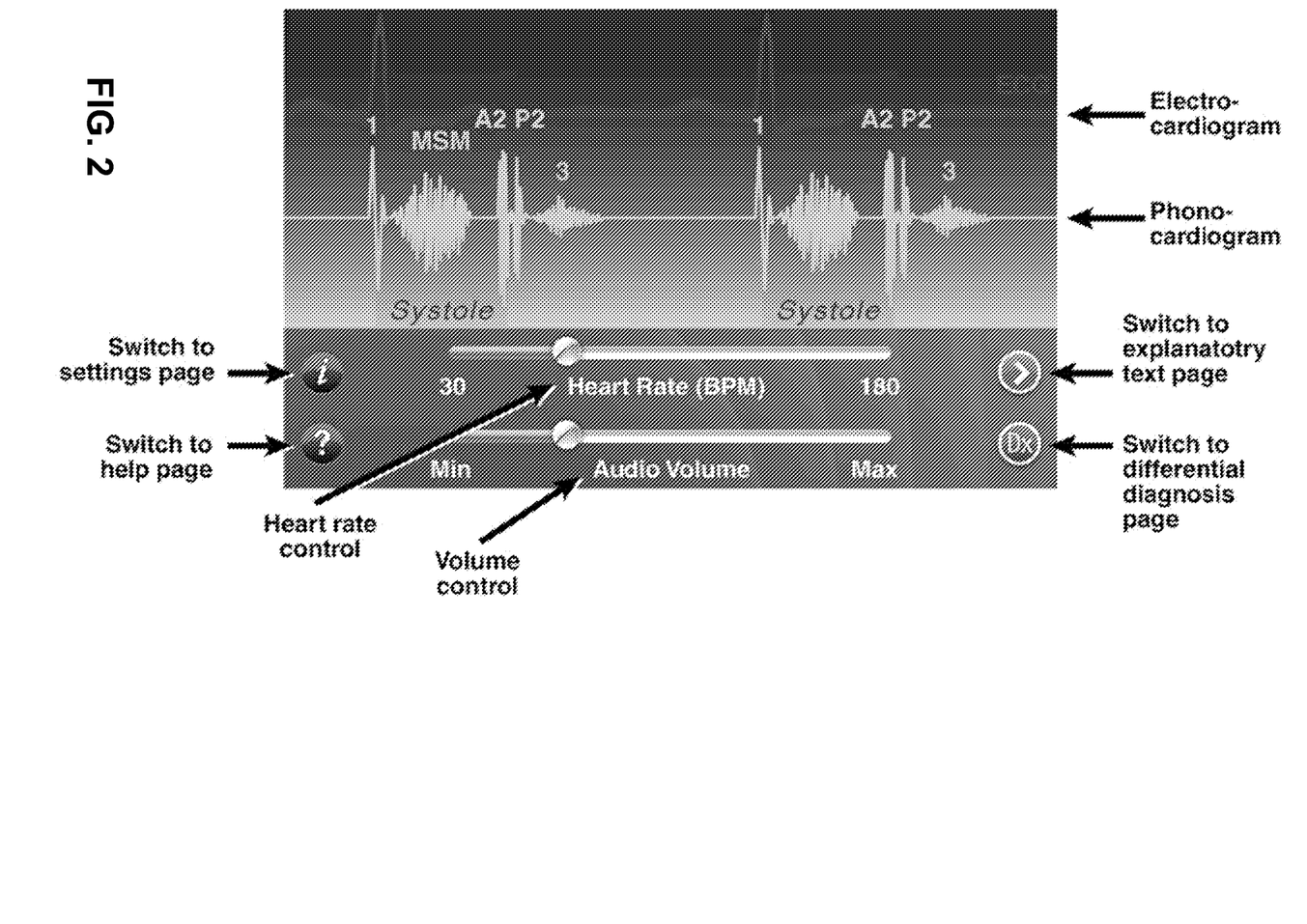
FIG. 2 is a graphical representation of a phonocardiogram created through the Sound Builder application and displayed with a corresponding ECG through a user interface according to various embodiments of the present invention.

FIG. 2 illustrates a sound sequence assembled from sound components, according to various embodiments of the invention. The sound sequence displayed shows the ECG, phonocardiogram, and the phases of the cardiac cycle, systole and diastole. Control buttons switch the display to settings, help, explanatory text, and the relevant differential diagnoses for this sound combination. Slider controls allow the user to vary the heart rate and the playback volume.

In some embodiments the Sound Builder application is configured to allow user control of heart rate, rhythm, and regularity. Heart rate can be varied to reflect different patient conditions, such as slower heart rates for relatively longer diastoles and faster heart rates for relatively shorter diastoles. Heart sounds and murmurs can be affected by changes in rhythm, for example, cannon wave, post-extrasystolic beat augments/does not augment murmurs, and atrial fibrillation (long or short diastoles). The frequency of the sound or murmur is not generally affected by the heart rate; for this reason, the rate may increase, but the sounds and murmurs themselves must be changed in temporal location (and often duration) without altering the frequency spectrum. Using discrete sound components allows the heart rate to be varied up or down without adversely affecting the frequency of the playback.

Figure 3:
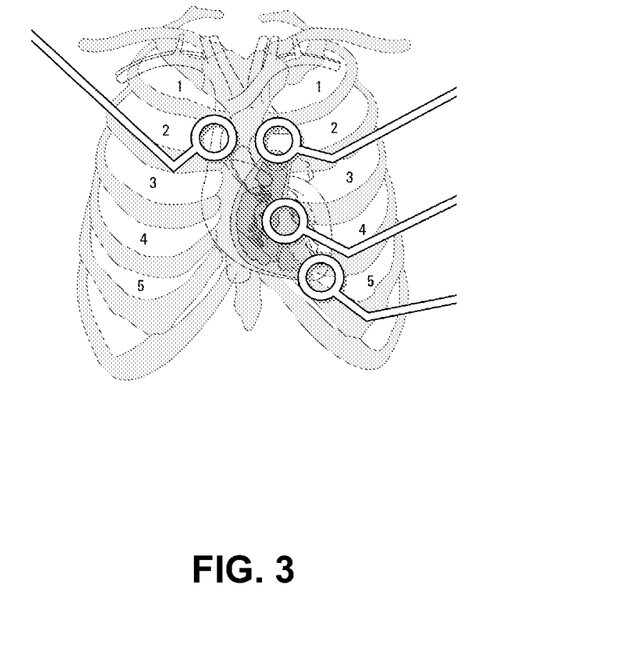
FIG. 3 is a schematic representation of common listening locations for stethoscopic cardiac examination.

FIG. 3 illustrates a chest diagram with circles indicating four common listening locations for a stethoscope during cardiac examination (other listening positions are possible). The numbers indicate intercostal spaces. Locations are generally noted as left or right, and by intercostal space. In the Sound Builder application, the location of the current heart sounds recording can be noted by this chest diagram, as well as alternate listening areas. For breath and lung sounds, a similar diagram is used. The user can change to a new listening position by selecting a different circle. In addition, if the user selects combinations that are specifically heard at one or two locations, the sound builder updates the displayed location to show where these sounds and murmurs would be heard. Manually switching to a new location will cause the sound/murmur combination to change what would be expected to be heard in a patient—in many cases removing the extra sound or murmur altogether.

As noted, the location of the stethoscope chest piece, and the choice of stethoscope bell or diaphragm, affects the loudness and quality of heart sounds and murmurs, and some sounds and murmurs are only detectable in specific locations on the patient's chest, and only with either the stethoscope bell or diaphragm. Also, the quality of the same murmur can be harsh or musical depending upon the location of the stethoscope. The location of the stethoscope can be indicated on the screen by text and/or by an indicator on a chest diagram. Switching to a different location will cause the selected sound combination to update. For example, moving from the cardiac apex (5th left intercostal at the midclavicular line) to the 2nd right intercostal space will cause S3 or S4 to disappear, and moving from the cardiac apex (5th left intercostal at the midclavicular line) to the 2nd left intercostal space will cause MDM and PSM to disappear.

The Sound Builder application can provide the user with an option of focusing on similar heart sounds and murmurs combinations while changing the location. For instance, extra sounds near S2 include S1 S2 OS (cardiac base), S1 Split S2 (cardiac base), and S1 S2 S3 (cardiac apex). Extra sounds near S1 include S1 ES S2 (cardiac apex or sometimes base), Split S1 S2 (cardiac apex), and S4 S1 S2 (cardiac apex).

The Sound Builder application is optionally configured to account for one or more of the following maneuvers and perturbations. The sound sequence can be varied depending on user-selectable factors such as respiration, posture, extrasystolic beat, hand grip, and Valsalva maneuver. Options for respiration include apnea, inspiration, and expiration, the latter two of which can augment murmurs, augment sounds, and split sounds. Posture options include supine, left lateral decubitus, sitting upright, sitting while leaning forward, standing, squatting, and passive leg elevation. The extrasystolic beat can augment or not augment the murmur. Hand grip options include control, grip, and release, while options for the Valsalva maneuver include control, strain, release, and recovery.

Figure 4:
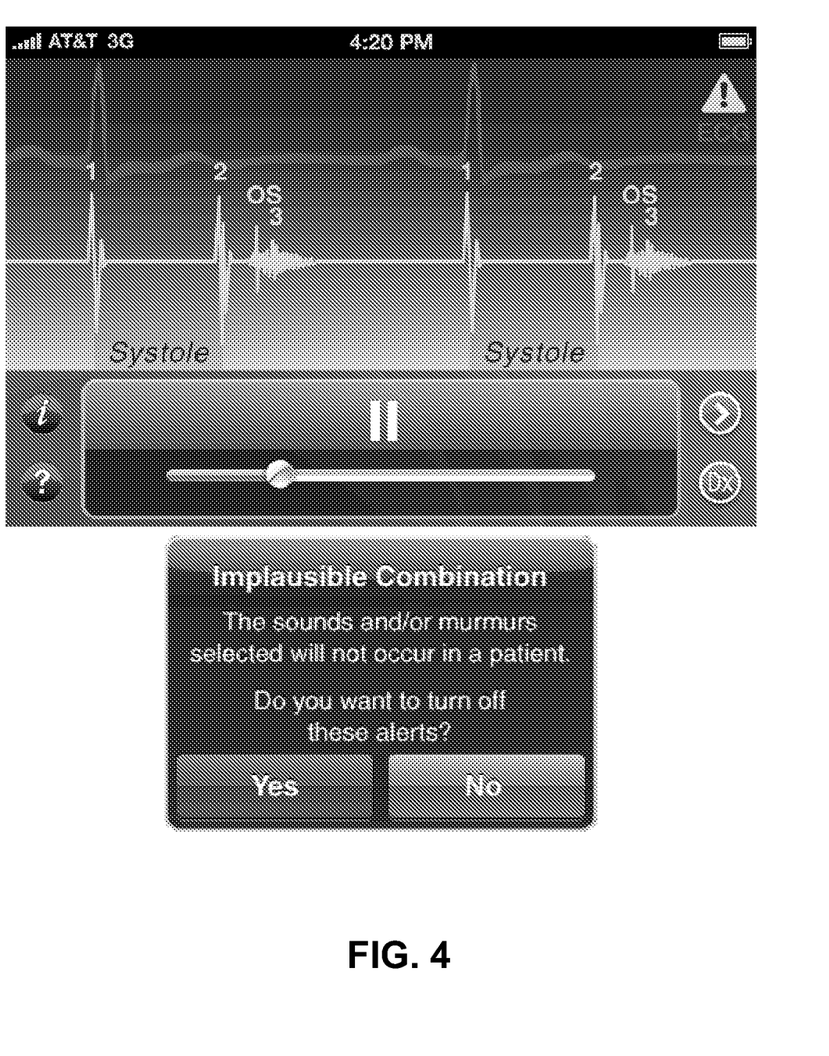
FIG. 4 is a graphical representation of an alert provided by the Sound Builder application and displayed through a user interface according to various embodiments of the present invention.

FIG. 4 illustrates an alert provided to the user through the Sound Builder interface when an implausible combination is selected, as not all combinations of heart sounds and murmurs are physiologically possible. An exemplary implausible combination is an opening snap (OS) and a third heart sound (S3). These sounds are not likely to occur simultaneously in a patient since the opening snap requires a narrowed, stenotic mitral valve, while a third heart sound usually requires a wide open mitral valve. In various embodiments a caution triangle appears in the sound display, and the user is alerted with a notice.

It is noted that with 20 heart sound and murmur components, there are an excessive number of possible combinations, but by limiting the combinations to only allowable combinations, a sounds and murmurs matrix includes 75,344 valid combinations. The Sound Builder application can automatically screen implausible selections by consulting a Sound-Murmur Plausibility Matrix, an example of which is shown below in Table 1. Adding more than one example of each murmur or sound will increase the combinations, but more importantly, increase the verisimilitude of the combinations. For example, the first heart sound of mitral stenosis is louder than normal; thus, a loud first heart sound of mitral stenosis would be substituted for a normal first heart sound. As another example, the midsystolic murmur of aortic stenosis can sound harsh when listening at the cardiac base, but musical at the cardiac apex.

TABLE 1

Allowed

| | S1a | S1b | S1S | S1c | S2a | S2b | S2S | ES | MSC | S3 | S4 | OS | HSM | ESM | MSM | LSM | EDM | MDM | PSM | CM |
|---|---|---|---|---|---|---|---|---|---|---|---|---|---|---|---|---|---|---|---|---|
| S1a | 1 | 0 | 0 | 0 | 1 | 0 | 0 | 0 | 1 | 0 | 1 | 1 | 1 | 1 | 0 | 1 | 1 | 1 | 1 | 1 |
| S1b | 0 | 1 | 0 | 0 | 0 | 1 | 1 | 0 | 0 | 0 | 0 | 0 | 0 | 0 | 1 | 0 | 0 | 0 | 0 | 0 |
| S1S | 0 | 0 | 1 | 0 | 0 | 1 | 1 | 0 | 1 | 0 | 1 | 1 | 1 | 1 | 0 | 1 | 1 | 1 | 1 | 1 |
| S1c | 0 | 0 | 0 | 1 | 1 | 0 | 0 | 1 | 0 | 0 | 0 | 0 | 0 | 0 | 0 | 0 | 0 | 1 | 0 | 0 |
| S2a | 1 | 0 | 0 | 1 | 1 | 0 | 0 | 1 | 1 | 1 | 1 | 0 | 1 | 0 | 1 | 1 | 1 | 1 | 1 | 1 |
| S2b | 0 | 1 | 1 | 0 | 0 | 1 | 0 | 0 | 1 | 0 | 0 | 0 | 0 | 0 | 1 | 0 | 0 | 0 | 0 | 0 |
| S2S | 0 | 1 | 1 | 0 | 0 | 0 | 1 | 1 | 1 | 1 | 1 | 0 | 1 | 0 | 1 | 1 | 1 | 1 | 1 | 1 |
| ES | 0 | 0 | 0 | 1 | 1 | 0 | 1 | 1 | 1 | 1 | 1 | 1 | 1 | 1 | 1 | 0 | 1 | 1 | 1 | 0 |
| MSC | 1 | 0 | 1 | 0 | 1 | 1 | 1 | 1 | 1 | 1 | 1 | 0 | 1 | 1 | 1 | 1 | 1 | 1 | 0 | 1 |
| S3 | 0 | 0 | 0 | 0 | 1 | 0 | 1 | 1 | 1 | 1 | 1 | 0 | 1 | 1 | 1 | 1 | 1 | 1 | 0 | 0 |
| S4 | 1 | 0 | 1 | 0 | 1 | 0 | 1 | 1 | 1 | 1 | 1 | 0 | 1 | 1 | 1 | 1 | 1 | 1 | 0 | 0 |
| OS | 1 | 0 | 1 | 0 | 0 | 0 | 0 | 1 | 0 | 0 | 0 | 1 | 1 | 0 | 1 | 0 | 0 | 1 | 1 | 0 |
| HSM | 1 | 0 | 1 | 0 | 1 | 0 | 1 | 1 | 1 | 1 | 1 | 1 | 1 | 0 | 0 | 0 | 1 | 1 | 1 | 0 |
| ESM | 1 | 0 | 1 | 0 | 0 | 0 | 1 | 1 | 1 | 1 | 1 | 0 | 0 | 1 | 0 | 0 | 1 | 1 | 0 | 0 |
| MSM | 0 | 1 | 0 | 0 | 1 | 1 | 1 | 1 | 1 | 1 | 1 | 0 | 0 | 0 | 1 | 0 | 1 | 1 | 0 | 0 |
| LSM | 1 | 0 | 1 | 0 | 1 | 0 | 1 | 0 | 1 | 1 | 1 | 0 | 0 | 0 | 0 | 1 | 1 | 1 | 0 | 0 |
| EDM | 1 | 0 | 1 | 0 | 1 | 0 | 1 | 1 | 1 | 1 | 1 | 0 | 1 | 1 | 1 | 1 | 1 | 0 | 0 | 0 |
| MDM | 1 | 0 | 1 | 1 | 1 | 0 | 1 | 1 | 1 | 1 | 1 | 1 | 1 | 1 | 1 | 1 | 0 | 1 | 1 | 0 |
| PSM | 1 | 0 | 1 | 0 | 1 | 0 | 1 | 0 | 0 | 0 | 1 | 1 | 0 | 0 | 0 | 0 | 0 | 0 | 1 | 0 |
| CM | 1 | 0 | 1 | 0 | 1 | 0 | 1 | 0 | 1 | 0 | 0 | 0 | 0 | 0 | 0 | 0 | 0 | 0 | 0 | 1 |
| TFA* | 0 | 1 | 1 | 0 | 1 | 0 | 1 | 0 | 0 | 0 | 0 | 1 | 1 | 0 | 1 | 0 | 1 | 1 | 0 | 0 |
| TFM* | 1 | 0 | 1 | 0 | 1 | 0 | 1 | 0 | 1 | 0 | 0 | 0 | 0 | 0 | 0 | 0 | 0 | 1 | 0 | 0 |

"1" is a valid combination;
"0" is an invalid combination

The user can look at and listen to (as well as palpate) the created combination. The Sound Builder application seamlessly loops the audio of the created combination, and the user may choose to listen via headphones, a wireless headset, an electronic stethoscope, or a wired or wireless speaker attached to an acoustic stethoscope, for example. While a loudspeaker can be used, it is noted that loudspeakers can distort audio.

The user can also observe the ECG waveform and the phonocardiogram, and also the selected buttons on the provided interface. The ECG waveform can indicate, for example, the onset of systole. The ECG waveform may morph, consistent with the sound-murmur combination selected. The phonocardiogram provides a visual depiction of heart sounds and murmurs and can be selected to show the selected combination, the actual heart sounds and murmurs of the patient, as well as cartoon depictions of idealized forms (no confusing artifacts), and to enhance recognition at small resolutions. The combination selected can be indicated, in some embodiments, by labeled buttons in an ON state (e.g., a white-colored button). The last button selected is optionally highlighted a different color (e.g., a yellow-colored button).

As noted, the user can palpate the created combination. In some embodiments, a signal to drive a palpable pulse will accompany the audio. Some embodiments provide a stereo output where one channel contains the audio and the other channel contains the pulse signal, including modulation and DC voltage. Locations include carotid (left or right), apical (apex beat), parasternal, brachial (left or right), radial (left or right), femoral (left or right), popliteal (left or right), and post tibial (left or right). Contour can include normal, quick, flicking upstroke, bounding, collapsing, slow rising, or distorted, when palpating pulse at peripheral vessels. These pulse contours can be displayed as waveforms or as audiovisual animations of the neck and precordium. Intensity and timing are additional options, where timing can be proximal to the heart (systolic rise occurs close in time with ventricular systole) or distal to the heart (systolic rise is delayed, and the pulse contour is distorted).

The user can compare the combination to the patient's heart sounds. For instance, by switching back and forth to the patient's heart sounds, the user can check whether the selected combination is a reasonable match to the patient's heart sounds. Two methods for making the comparison involve either switching ear pieces or not switching ear pieces. Where switching ear pieces is employed, the Sound Builder application plays the selected audio combination and a stethoscope or playback device plays the patient's heart sounds on a separate system. Alternatively, the Sound Builder application can be switched between playing the selected audio combination through a set of ear pieces and either a live transmission or a recording of the patient's heart sounds. In another alternative, the Sound Builder system includes an external speaker, and the user moves the stethoscope between the patient's chest and the external speaker to make the comparison.

A good match with the patient will not require further modification of the combination. A poor match will prompt the user to modify his selected combination. Errors in understanding the definitions can lead to erroneous selections, for example, the user may confuse a continuous murmur with a to-fro murmur. Failure to identify systole can also lead to erroneous selections, for instance, the user may confuse a systolic murmur with a diastolic murmur.

In various embodiments the Sound Builder application provides an info section that the user can access by pressing the info button, for instance, in order to learn more about each sound/murmur choice. The first page displayed in the info section can be linked to the last button the user selected on the control panel. Additional pages that describe other control panel choices can be made available from a table of contents, or by pressing previous or next buttons.

Similarly, various embodiments the Sound Builder application provide a help section that can be accessed, for example, by pressing the help button to display the help section on the screen. The help section can provide a description each button's appearance and function, program flow, a description of each section, the role of the differential diagnosis section (including limitations and when alternative diagnoses should be considered), recommended customized settings based on the user's preferences, and cardiac examination tips and tricks to improve detection and identification of findings.

Various embodiments the Sound Builder application can also provide the user the ability to customize certain settings. Examples of customizable settings include the display, warnings, and preferences for sending and receiving data.

The Sound Builder application can also provide the user the ability to modify a combination to create a closer match to the patient's sounds, for example, through an interactive process, possibly over several iterations, of selecting a combination, comparing the combination to the patient, and modifying the combination, to hone in on a best match to the patient findings.

The Sound Builder application can also offer plausible alternatives to aid in the step of modifying the combination. For instance, sound combinations near S1 and S2 are often confused, heart sounds are often not heard when a murmur is present, systolic murmurs are often confused, diastolic murmurs are often confused, continuous murmurs are often confused with to-fro murmurs, certain sound/murmur combinations are commonly confused, and confusion of systole and diastole leads to a large number of errors.

Regarding sound combinations near S1, the combinations of S4 and S1, split and S1, S1 and ES, S1 and early MSC are commonly confused. Regarding sound combinations near S2, the combinations of late MSC and S2, split and S2, S2 and OS, and S2 and S3 are commonly confused. Heart sounds that are often not heard when a murmur is present include S1 and S2 with HSM, S3 with HSM or another murmur, and MDM/S3 rumble with EDM (Austin Flint).

Systolic murmurs that are often confused include MSM vs. HSM. Here, right-sided murmurs may in fact be midsystolic, but run into or past the aortic valve closure sound (usually the loudest component of S2) tricking the user into thinking the murmur is holosystolic. An ejection sound (ES) may precede the MSM, tricking the user into thinking the murmur begins with S1, and concluding the murmur is ESM or HSM. Crescendo-decrescendo holosystolic murmurs are possible, and may confuse the user who expects this shape of murmur to be exclusively midsystolic. Other systolic murmurs that are often confused include MSM vs. ESM (both end before S2), LSM vs. MSM vs. HSM (regurgitation following the click of mitral valve prolapse), and musical murmurs (Gallavardin) which are often considered different in origin from harsh murmurs, when in fact they have the same etiology.

Diastolic murmurs that are often confused include EDM vs. MDM, EDM long vs. CM, and EDM with MDM (Austin Flint) vs. EDM. Sound/murmur combinations that are often confused include S1 MSC LSM S2, S1 ES MSM S2, and S4 S1 HSM S2.

The best match result of this refinement process may be definitive or may contain ambiguous features. In the latter instance, for example, the user may not be able to determine whether an extra sound near S1 is S4-S1, S1-ES, or a split S1. Over-specificity may not be appropriate when the findings cannot be firmly established, and alternative findings can be stored with equal weight, or with preferential weights assigned to the alternatives.

Figure 5:
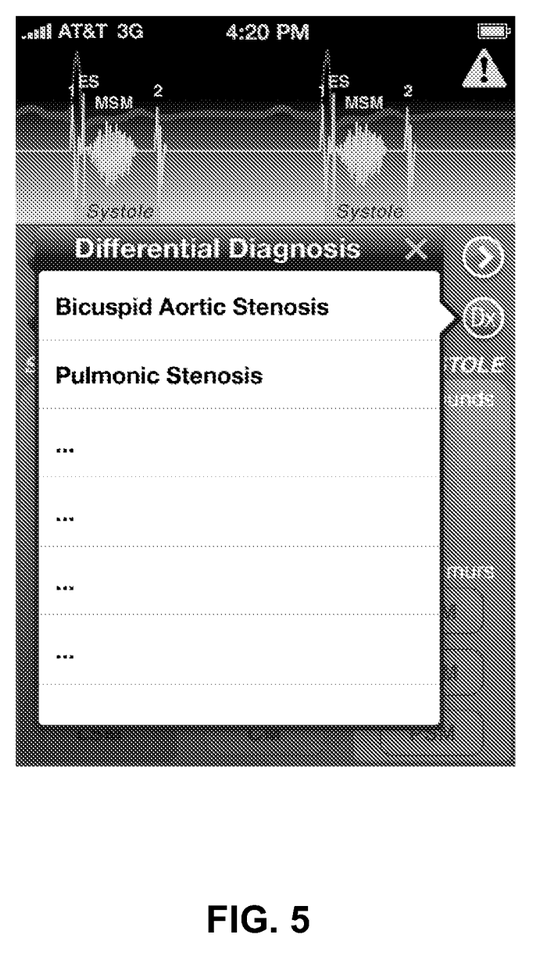
FIG. 5 is a graphical representation of a differential diagnosis screen provided by the Sound Builder application and displayed through a user interface according to various embodiments of the present invention.

FIG. 5 illustrates a differential diagnosis list that can be provided to the user as a list of potential differential diagnoses based on the final combination entered. The Dx button turns green, in some embodiments, to indicate that the list of potential diagnoses has become very narrow. In the illustrated example, S1 ES MSM S2 has a short list of potential diagnoses, either bicuspid aortic stenosis or aortic stenosis. The Sound Builder application can help narrow the choices further with queries to the user. For example, the user can be asked to report the contour of the carotid pulse (for aortic stenosis the pulse is parvus et tardus), to compare 2nd right vs. 2nd left intercostal listening areas, or the user can be prompted to learn more about the clinical setting by suggesting interview questions for the patient.

The Sound Builder application may create the Dx list by consulting a Sounds-Murmurs Dx Matrix that contains likely diagnoses mapped to the selected sounds and murmurs. This list of differential diagnoses can be dynamically updated based upon further input from the user, including listening location, patient history, and vital signs (e.g., pulse contour, heart rate, body temperature, blood pressure). Patient history can comprise the patient's chief complaint, social history (e.g., smoking, IV drug abuse), any childhood illness, and country of origin (e.g., where rheumatic fever is still prevalent). The Dx list can be sorted by plausibility, or severity, and each Dx entry can be linked to explanatory text, illustrations, and audio or audiovisual examples of patient recordings.

The Sound Builder application, in some embodiments, suggests additional actions to narrow the differential diagnosis, including altering the listening location, switching from stethoscope bell to diaphragm, postural maneuvers, and the postextrasystolic beat. Altering the listening location can help, for example, to differentiate between whether an extra heart sound near S1 is an S4, a split S1, or an ejection sound. If the extra sound is heard at locations in addition to the cardiac apex, it is likely to be an ejection sound, with a softer S1 preceding it. Likewise, listening at the apex with the stethoscope bell will most likely detect the low-frequency S4, but switching to the stethoscope diaphragm (which filters low frequency sounds) should make the extra sound go away.

Postural maneuvers can help detect the midsystolic click of mitral valve prolapse which can occur earlier or later as a function of standing and squatting and as a function of the Valsalva maneuver. The postextrasystolic beat (the beat that follows a preventricular contraction, or PVC) can narrow the origin of a systolic murmur. Systolic murmurs that augment following a PVC are generally confined to the ventricular outflow tract such as aortic stenosis and hypertrophic cardiomyopathy, while systolic murmurs that do not augment include the holosystolic murmur of mitral regurgitation.

The Sound Builder application, in some embodiments, suggests items in the patient's history or the clinical setting to investigate to narrow further the differential diagnosis. As examples, a patient presenting with worsening dyspnea during pregnancy suggests mitral stenosis, while being from certain areas of the world (e.g., the Pacific Rim and Latin America) can implicate rheumatic fever. As another example, aortic regurgitation secondary to endocarditis can be due to IV drug abuse with infected needles. As yet another example, a third heart sound can be physiologic or pathologic in origin, where a physiologic third heart sound is common in athletes, the healthy young, and pregnancy, while a pathologic third heart sound can be due to ventricular dysfunction secondary to myocardial infarction, hypertension, or dilated cardiomyopathy.

The Sound Builder application can assist the user to document the patient's cardiac examination findings by appending the patient name, ID number, location (of the patient), time and date to the findings, and by adding the patient's history, vital signs, and other patient data. Listening location can be added by selecting a listening area off of a chest diagram. The examination findings can indicate that the final selection satisfied the user that these are the findings established upon examination of the patient, or may indicate that the final selection contains appropriate ambiguity where a finding cannot be firmly established. Documented findings can be uploaded securely with encryption to a database that stores the patient's electronic health record.

In some instances, the Sound Builder application can be used in reverse by using a lesion-based menu on the control panel. Here, the user starts with a diagnosis, and the Sound Builder application then reproduces the spectrum of findings associated with that lesion for comparison against the patient. For instance, selecting congenital aortic stenosis will cause the application to produce the pattern of S1, ES, MSM, S2, while selecting calcific aortic stenosis will cause the application to produce the pattern of S1, MSM, S2. Similarly, selecting well-tolerated chronic aortic regurgitation will cause the application to produce long EDM, selecting acute severe aortic regurgitation will produce short EDM, MSM, S1 (soft or absent), and selecting Austin Flint aortic regurgitation will produce, in addition to the sounds of acute severe aortic regurgitation, MDM at the apex.

Mitral stenosis and regurgitation provide additional examples. Mitral stenosis may be tolerated by the patient at a slow heart rate, become more severe with moderate heart rate, or very severe with fast heart rate. Tolerated mitral stenosis is indicated by an opening snap and a barely detectable mid diastolic murmur. The more severe mitral stenosis is indicated by loud S1, MDM, perhaps no PSM, and longer S2-OS interval. The very severe mitral stenosis is indicated by a louder and later S1, PSM, MDM, and short S2-OS interval.

The Sound Builder application optionally may be configured to facilitate methods to improve identification of individual sound components. As one example, by adding and removing a single component to highlight its presence or absence against the background of other sounds and murmurs. With S1 S2 S3, often the user does not perceive the low-frequency, low-intensity S3, thus, by adding and removing S3 while S1 and S2 remain can improve detection by giving the user a visual cue when S3 is present on the phonocardiogram, as well as by playing the extra sound. As another example, positional audio processing can be employed to place components in three-dimensional space, so that the user can perceive some sounds as occurring in front, to the side, or behind the ears. Human hearing is very sensitive to positional cues that occur as sounds are modified as they reflect off external surfaces, as well as the portions of the external ear. In addition, subtle differences in frequency and arrival time to both ears give the brain cues as to the location of a particular sound. These audio cues can be added to existing audio with head-related transfer functions (or similar methods) to create the perception that a particular sound is emitting from a certain position in space. For example, positioning the audio location of S1 and S2 behind the user's head, and positioning the murmurs in front, can help the user identify the sounds, and differentiate them from the murmurs. Likewise, the presence of an extra heart sound can be highlighted by placing the extra sound in yet another position (e.g., left or right). Merging the sounds and murmurs back into monoaural space will reflect what is heard through the stethoscope, while expanding the sounds to highlight components aids in their identification. Another aid in identification is matching visual information (either video of patient or computer animation of an avatar) to the sounds, to aid in recognition. Human hearing becomes more sensitive and specific if a sound is accompanied by a visual cue. Animation or video of pulsations in the neck or precordium, or movement of the chest during respiration, when displayed in time with the heart and lung sounds, will aid the user in identifying individual sound components.

The Sound Builder application can also comprise a lung sounds builder module that functions analogously and with the same technology as the heart sounds builder module illustrated above, but employing breath sounds components. Here, the user listens to the patient's chest for lung sounds and consults the lung sounds builder to select lung sound components in order to create a matching combination. The user can also select different patient postures (e.g., supine, upright), respiratory patterns (normal, tachypnea, Cheyne-Stokes), or patient maneuvers (e.g., egophony). The user then compares the selected combination with the patient's lung sounds and modifies the selected combination as necessary to improve the match to the patient's lung sounds. The lung sounds builder is configured to suggest differential diagnoses based on the combination selected. In various embodiments, the lung sounds builder suggests additional listening locations, maneuvers, and items in the patient's history or clinical setting to narrow further the differential diagnosis. In various embodiments, the lung sounds builder can be used in reverse: starting with a condition, and playing back the spectrum of lung sounds that are associated with the selected patient condition.

In the foregoing specification, the invention is described with reference to specific embodiments thereof, but those skilled in the art will recognize that the invention is not limited thereto. Various features and aspects of the above-described invention may be used individually or jointly. Further, the invention can be utilized in any number of environments and applications beyond those described herein without departing from the broader spirit and scope of the specification. The specification and drawings are, accordingly, to be regarded as illustrative rather than restrictive. As used herein, logic refers to hardware, firmware, or a combination of hardware and software such as a processor and computer readable instructions stored on a computer readable medium, but logic as used herein specifically excludes software alone. It will be recognized that the terms "comprising," "including," and "having," as used herein, are specifically intended to be read as open-ended terms of art.

What is claimed is:

1. A method comprising:
   selecting, using an input device of a computing system, a first bodily sound component from a menu of sound components;
   selecting, using the input device, a second bodily sound component from the menu of sound components, the first and second bodily sound components being representative of first and second sounds of a stethoscopic examination;

observing on a display of the computing system, and listening to, a repeating graphical representation of the first and second sound components; and simulating an abnormality by iteratively modifying and observing the graphical representation.

2. The method of claim 1 wherein the first bodily sound component is a first lung sound component and wherein the second bodily sound component is a second lung sound component.

3. The method of claim 2 wherein selecting the first and second bodily sound components from the menu of sound components comprises selecting a respiratory pattern from a menu of respiratory patterns.

4. The method of claim 1 wherein the graphical representation of the first and second sound components comprises a phonocardiogram.

5. The method of claim 1 wherein modifying the graphical representation comprises selecting a third sound.

6. The method of claim 1 wherein modifying the graphical representation comprises changing a relative timing of the first and second sounds.

7. The method of claim 1 further comprising an act of reading a list, the list including the names of differential diagnoses, the list being read from the display of the computing system.

8. The method of claim 4 further comprising viewing on the display of the computing system an ECG proximate to the graphical representation of the first and second sound components.

9. The method of claim 1 wherein listening to the repeating graphical representation of the first and second sound components includes hearing the first and second sound components spatially separated from one another.

10. The method of claim 4 wherein the first and second sounds are heart sounds S1 and S2.

11. The method of claim 1 further comprising physically examining a patient, wherein the first and second sound components are selected to be representative of first and second sounds heard during a stethoscopic examination of the patient.

12. The method of claim 11 further comprising uploading, from the computing system, findings from the physical examination to an electronic health record for the patient.

* * * * *